United States Patent [19]

Kurze et al.

[11] Patent Number: 4,846,837
[45] Date of Patent: Jul. 11, 1989

[54] CERAMIC-COATED METAL IMPLANTS

[75] Inventors: Peter Kurze, Oberlichtenau; Waldemar Krysmann, Karl-Marx-Stadt; Wolfram Knoefler; Hans-Ludwig Graf, both of Leipzig, all of German Democratic Rep.

[73] Assignee: Technische Universitaet Karl-Marx-Stradt, Karl-Marx-Stadt, German Democratic Rep.

[21] Appl. No.: 196,851

[22] Filed: May 16, 1988

Related U.S. Application Data

[63] Continuation of Ser. No. 938,696, Dec. 5, 1986, abandoned.

[30] Foreign Application Priority Data

Feb. 12, 1986 [DD] German Democratic Rep. .................................... 2869733

[51] Int. Cl.$^4$ .......................... A61F 2/28; C25D 11/00
[52] U.S. Cl. ......................................... 623/16; 623/66; 204/56.1
[58] Field of Search .................. 204/56.1; 623/16, 22, 623/23, 66; 433/201.1

[56] References Cited

U.S. PATENT DOCUMENTS

| | | | |
|---|---|---|---|
| 3,956,080 | 5/1976 | Hradcovsky et al. | 204/56.1 X |
| 4,309,488 | 1/1982 | Heide et al. | 428/547 |
| 4,483,678 | 11/1984 | Nishio et al. | 623/18 X |
| 4,495,664 | 1/1985 | Blanquaert | 623/23 |

FOREIGN PATENT DOCUMENTS

| | | | |
|---|---|---|---|
| 0042783 | 12/1981 | European Pat. Off. | 623/16 G |
| 0158651 | 1/1983 | Fed. Rep. of Germany | 204/56.1 |
| 0534525 | 11/1973 | U.S.S.R. | 204/56.1 |
| 0962904 | 7/1964 | United Kingdom | 204/56.1 |
| 8606617 | 11/1986 | World Int. Prop. O. | 623/66 |

*Primary Examiner*—Alan W. Cannon
*Attorney, Agent, or Firm*—Jordan and Hamburg

[57] ABSTRACT

A ceramic-coated metal implant is used in medicine as a hemiprosthesis or endoprosthesis. A metal implant base body having at least a surface comprised of a barrier layer metal is imparted with a surface roughness of 100–400 $\mu$m by means of a mechanical and/or chemical and/or electrochemical pretreatment, thereby increasing the effective surface by more than 400%. Using anodic oxidation through spark discharge in aqueous electrolytes, an outer thickness of the roughened barrier layer metal is converted into a ceramic layer comprising oxides of the barrier layer metal and, optionally, a resorbable calcium phosphate. A maximum amount of calcium phosphate ceramic in the oxide layer faces an implantation bed of the implant. The calcium phosphate ceramic concentration decreases in the direction towards the phase boundary of the base body and oxide layer, so that bone can grow into the ceramic-coated metal implant and attain a high tenacity. In order to attain characteristics which are specific to bone, an after treatment in specific media, such as, for example, amino acids or antibiotics, can be performed. The implant can remain in place for a long period, is highly compatible with tissue and provides a large surface of bone contact, which automatically regulates bone growth in accordance with healing and growth processes.

2 Claims, No Drawings

CERAMIC-COATED METAL IMPLANTS

This application is a continuation of application Ser. No. 938,696, filed Dec. 5, 1986, abandoned.

BACKGROUND OF THE INVENTION

The invention relates to a ceramic-coated metal implant for use in medicine a hemiprosthesis and endoprosthesis.

Known implants are made out of metals or metal alloys, such as titanium, tantalum, chromium-cobalt-molybdendum alloys and materials such as carbon, polymers or alumminum oxide ceramics or combinations thereof.

An improvement of the characteristics of an implant has been attempted by means of specific surface treatments. In DE-OS No. 2,324,867 the biocompatibility of a metal implant is temporarily improved by storing ions in the surface of the metal implant. Due to diffusion, however, a short time after implanting, harmful ions enter into the implant bed and, thus, it cannot be assured that the implant will stay in place for a long time.

DE-OS No. 2,838,759 has the aim of rendering the surface of an implant passive by means of sophisticated vacuum techniques. layers applied with this technique are very thin and do not adhere very well and, thus, have a negative influence on the in-situ period for the implant.

EP No. 0023608 describes a bioreactive calcium phosphate ceramic which is pressed onto the surface of a metallic implant body by a pressing-sintering process. EP No. 006544 introduces an implantable metallic bone material on the surface of which spherical calcium phosphate particles are applied. This is achieved in that a calcium phosphate particles are adhered to the inside walls of mold which is then filled with metal. The same effect can be achieved by hot-pressing, flame-spraying or plasma-spraying.

The calcium phosphate ceramic applied in this way, however, can easily be leached out in the living body and, furthermore, is insufficiently adjusted to bone growth in its concentration supply and does not take into consideration required textural dimensions in order for tissue to grow into it. The period during which the implant can remain in place is therefore negatively influenced.

The literature (Strauss, V.E. Bild der Wissenschaft 2 (1984), 110–122) describes a compound ceramic-metal implant. The advantages of the ceramic should be simultaneously combined with the strength of the metal. The applied ceramic layers, however, do not sufficiently adhere to the metal. The surgically inserted implant is, therefore, severely limited as to the period during which it can stay in place.

SUMMARY OF THE INVENTION

An object of the invention is to provide a cost-effective metal implant which has a long period during which it can remain in place and is highly compatible with tissue and bone.

Another object of the invention is to provide a metal implant which is provided with an enlarged surface vis-a-vis an implant bed and which automatically regulates bone growth according to the healing and growing processes.

According to the invention, the object are attained in that a metal implant base body having a barrier layer metal or alloy thereof or a metal coated with a barrier layer metal or alloy thereof is subjected to a defined mechanical and/or chemical and/or electrolytic texturing, so that a surface roughness of 100 $\mu$m to 400 $\mu$m increases the effective surface by more than 400%. Onto this metal implant base body is applied a ceramic having a thicknesss of 5–30 $\mu$m and grain dimensions of 2–20 $\mu$m diameter, which is composed of a layer up to 100% of briefly molten oxides of the metal or metals of the implant base body comprised of nonstoichiometric oxides and mixed oxides or of 90% to 60% of these oxides and 10% to 9% calcium phosphate ceramic. Thereby reposes a concentration distribution of the calcium phosphate ceramic up to almost the phase boundary between the metal implant base body/ceramic < 1 $\mu$m, whereby the maximum supply of the calcium phosphate ceramic lies on a side facing the implantation bed.

DETAILED DESCRIPTION OF THE PREFERRED EMBODIMENTS

According to the invention, the calcium phosphate ceramic deposit definedly dispersed in the oxide layer determines the healing and growth processes and the adhesion of the bone to the coated metal implant because at the phase boundary of the side of the oxide layer facing the metal implant base body in a zone of less than 1 $\mu$m there is no resorbable calcium phosphate ceramic.

According to the invention, due to the resorption process, the bone grows into the ceramic-coated metal implant providing for the bone contacts required for great adhesion, wherein the surface formation of the bone contacts automatically controls the utilization of the supply of resorbable calcium phosphate ceramic in correspondence with the distribution of stress. Therefore, no locations are formed without bone contacts.

The production of the ceramic-coated metal implant usually takes place in a one-step process. In order to produce characteristics which are specific to tissue or bone, it is possible to perform an after-treatment in specific media, such as, for example, amino acids or antibiotics.

The invention will be explained in greater detail by example.

A metal implant comprised a titanium, for example, a hip-joint endoprosthesis, is subjected to a mechanical texturing by means having jet treatment with superrefined corundum of a grain size of 100 to 200 $\mu$m for 5 minutes and is then exposed to a chemical etching in a 55% hydrofluoric acid solution. Surface layer scanning and microscopic measurements show structural dimensions of 150 to 280 $\mu$m.

Subsequent anodic oxidation under spark discharge in an aqueous solution of complex-bound calcium phosphate and dispersed tri- and tetracalcium phosphate leads under pulse voltage to a 12 $\mu$m thick briefly molten layer of titanium oxides comprised of nonstoichiometric oxides and mixed oxides, having grain dimensions of 6 $\mu$m and comprising a calcium phosphate ceramic proportion of 27% on the side facing the implant bed.

The implants treated in accordance with the invention exhibit upon implantation onto or into bone an approximately 15% increased portion of direct bone contacts.

We claim:

1. A method of preparing an implant comprised of a ceramic-coated metal and which is highly compatible with tissue and bone, comprising texturing a surface of an implant base body which surface is comprised of a barrier layer metal to impart thereto a surface roughness of 100 to 400 μm, thereby increasing the effective surface by more than 400%, and then subjecting said barrier layer metal to anodic oxidation under spark discharge in an aqueous electrolyte solution containing calcium phosphate thereby to convert the outer 5 to 30 μm thickness thereof to a ceramic comprised 90 to 60% of oxides of the barrier layer metal and 10 to 40% of calcium phosphate and having grain dimensions of 2 to 20 μm diameter, said oxides briefly being molten during the anodic oxidation under spark discharge, the calcium phosphate being of a concentration distribution wherein the concentration decreases from a maximum at a surface of the ceramic coating to essentially zero within 1 μm of a phase boundary between the ceramic coating and underlying barrier layer metal.

2. An implant which is highly biocompatible with tissue and bone, comprising a metallic base body having a textured surface comprising a barrier layer metal, said textured surface having a surface roughness of 100 to 400 μm and being ceramic-coated by the method of claim 1, such that the outer 5 to 30 μm thickness thereof are comprised of 90 to 60% of oxides of said barrier layer metal and 10 to 40% of calcium phosphate and have grain dimensions of 2 to 20 μm diameter, the calcium phosphate concentration distribution being such that said concentration decreases from a maximum at a surface of the ceramic coating to essentially zero within 1 mm of a phase boundary between said ceramic coating and said barrier layer metal.

* * * * *